United States Patent
Lee et al.

(10) Patent No.: US 10,869,745 B2
(45) Date of Patent: Dec. 22, 2020

(54) TISSUE MATRIX WITH PREFORMED OPENINGS OR PILOT OPENINGS

(71) Applicant: LifeCell Corporation, Branchburg, NJ (US)

(72) Inventors: Dennis Y. Lee, Scotch Plains, NJ (US); Jennifer Lynn Steinkoenig, Basking Ridge, NJ (US); Israel James Jessop, Annandale, NJ (US); Alexander Ringo, Somerset, NJ (US)

(73) Assignee: LifeCell Corporation, Madison, NJ (US)

( * ) Notice: Subject to any disclaimer, the term of this patent is extended or adjusted under 35 U.S.C. 154(b) by 329 days.

(21) Appl. No.: 15/724,616

(22) Filed: Oct. 4, 2017

(65) Prior Publication Data

US 2018/0098836 A1 Apr. 12, 2018

Related U.S. Application Data

(60) Provisional application No. 62/404,815, filed on Oct. 6, 2016.

(51) Int. Cl.
*A61F 2/00* (2006.01)

(52) U.S. Cl.
CPC .............. *A61F 2/00* (2013.01); *A61F 2/0063* (2013.01); *A61F 2/0077* (2013.01); *A61F 2002/0068* (2013.01)

(58) Field of Classification Search
CPC .................. A61F 2/0063; A61F 2/0077; A61F 2002/0081; A61F 2002/0068; A61F 2013/00251; A61F 2013/00255; A61F 2013/00357; A61F 2013/00089; A61L 2430/34; A61L 2430/40; A61L 27/3633; A61L 27/60
See application file for complete search history.

(56) References Cited

U.S. PATENT DOCUMENTS

| 3,902,198 A | 9/1975 | Cooper |
| 5,290,217 A * | 3/1994 | Campos ............... A61F 2/0063 128/897 |

(Continued)

FOREIGN PATENT DOCUMENTS

| WO | 1997/06837 A1 | 2/1997 |
| WO | 2007/004214 A2 | 1/2007 |

(Continued)

OTHER PUBLICATIONS

Adelman et al., Bovine versus Porcine Acellular Dermal Matrix: A Comparison of Mechanical Properties. Plastic and Reconstructive Surgery Global Open. May 15, 2014;e155; doi:10.1097/GOX.0000000000000072. 7 pages.

(Continued)

*Primary Examiner* — Melanie R Tyson
(74) *Attorney, Agent, or Firm* — McCarter & English, LLP

(57) ABSTRACT

The present disclosure relates to tissue matrix products. The products can include tissue matrices that have openings such as holes or perforations located at certain positions to improve various functions without substantial loss of strength or other important properties. The openings can facilitate implantation of the tissue matrices in surgical procedures thereby speeding operation times and potentially improving surgical results.

30 Claims, 14 Drawing Sheets

(56) References Cited

U.S. PATENT DOCUMENTS

| | | | |
|---|---|---|---|
| 5,433,996 A * | 7/1995 | Kranzler | B32B 7/12 |
| | | | 442/40 |
| 6,039,686 A * | 3/2000 | Kovac | A01H 5/02 |
| | | | 600/30 |
| 6,355,065 B1 * | 3/2002 | Gabbay | A61F 2/0045 |
| | | | 606/151 |
| 7,105,001 B2 * | 9/2006 | Mandelbaum | A61B 17/08 |
| | | | 128/898 |
| 8,049,059 B2 | 11/2011 | Bleyer et al. | |
| 8,323,352 B2 | 12/2012 | Friedman et al. | |
| 8,323,701 B2 | 12/2012 | Daniel et al. | |
| 8,986,377 B2 | 3/2015 | Richter et al. | |
| 9,114,003 B2 | 8/2015 | Kalus | |
| 9,351,819 B2 | 5/2016 | Harper | |
| 9,888,924 B2 * | 2/2018 | Ebersole | A61B 17/07207 |
| 2004/0034374 A1 | 2/2004 | Latzsch et al. | |
| 2007/0088434 A1 | 4/2007 | Frank | |
| 2009/0082864 A1 | 3/2009 | Chen et al. | |
| 2009/0281559 A1 * | 11/2009 | Swain | A61B 17/1114 |
| | | | 606/153 |
| 2010/0191044 A1 * | 7/2010 | Gobron | A61B 17/0401 |
| | | | 600/37 |
| 2011/0166673 A1 | 7/2011 | Patel et al. | |
| 2011/0208320 A1 * | 8/2011 | Stevenson | A61B 17/08 |
| | | | 623/23.72 |
| 2012/0158134 A1 | 6/2012 | Codori-Hurff et al. | |
| 2012/0269780 A1 * | 10/2012 | Marzaro | A61L 27/3691 |
| | | | 424/93.7 |
| 2012/0283826 A1 | 11/2012 | Moses et al. | |
| 2013/0204077 A1 * | 8/2013 | Nagale | A61F 2/0063 |
| | | | 600/37 |
| 2014/0100655 A1 | 4/2014 | Diaz et al. | |
| 2015/0032167 A1 * | 1/2015 | Heino | B29B 11/10 |
| | | | 606/284 |
| 2015/0157451 A1 | 6/2015 | Bowley et al. | |
| 2015/0320911 A1 * | 11/2015 | Sun | A61L 31/06 |
| | | | 604/540 |
| 2016/0045198 A1 | 2/2016 | Bachrach | |
| 2017/0072110 A1 | 3/2017 | Ringo | |

FOREIGN PATENT DOCUMENTS

| | | |
|---|---|---|
| WO | 2012/166784 A1 | 12/2012 |
| WO | 2014/008184 A1 | 1/2014 |
| WO | 2017/044682 A1 | 3/2017 |

OTHER PUBLICATIONS

Burger et al., Incisional hernia: early complication of abdominal surgery. World J Surg. Dec. 2005;29(12):1608-13.

Cavallo et al., Remodeling characteristics and biomechanical properties of a crosslinked versus a non-crosslinked porcine dermis scaffolds in a porcine model of ventral hernia repair. Hernia. Apr. 2015;19(2):207-218.

Deerenberg et al., Small bites versus large bites for closure of abdominal midline incisions (STITCH): a double-blind, multicentre, randomised controlled trial. Lancet. Published online Jul. 16, 2015. 7 pages.

Gaumann et al., The anatomic basis of the transversus and rectus abdominis musculoperitoneal (TRAMP) composite flap. Hernia. Feb. 1999;3:39-41.

Goodenough et al., Development and validation of a risk stratification score for ventral incisional hernia after abdominal surgery: hernia expectation rates in intra-abdominal surgery (the Hernia Project). J Am Coll Surg. Apr. 2015;220(4):405-13.

Pollock et al., Early prediction of late incisional hernias. Br J Surg. Sep. 1989;76(9):953-4.

Tsuda, Laparoscopic repair of complicated umbilical hernia with Strattice Laparoscopic™ reconstructive tissue matrix International Journal of Surgery Case Reports. Nov. 2014;5:1167-1169.

International Search Report and Written Opinion for Application No. PCT/US2017/055053, dated Jan. 25, 2018. 16 pages.

* cited by examiner

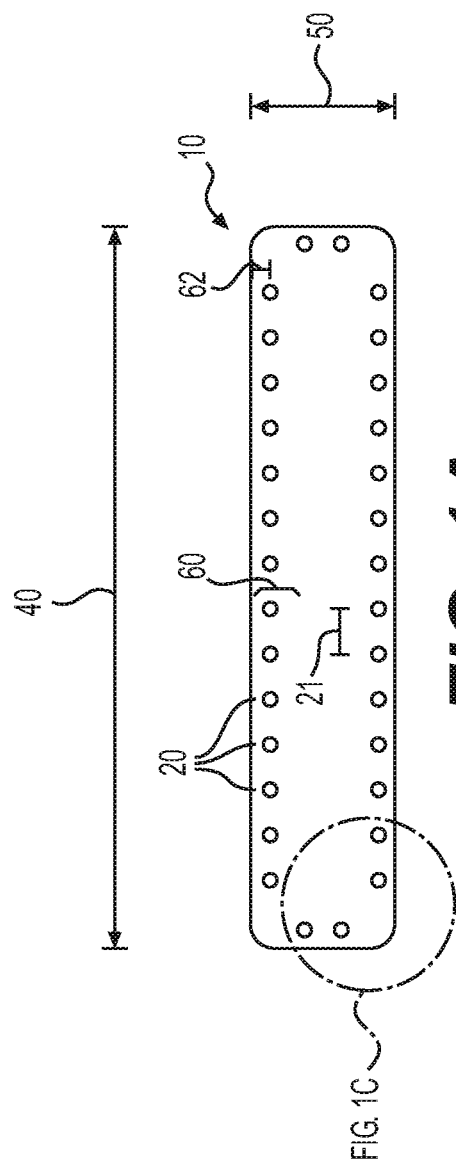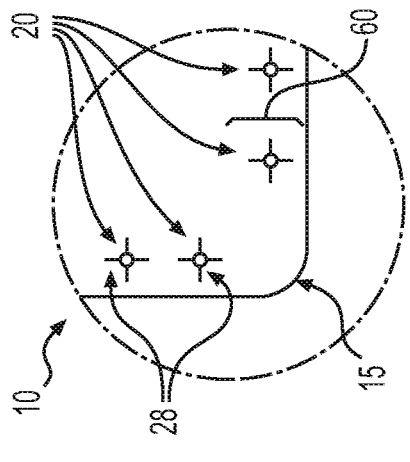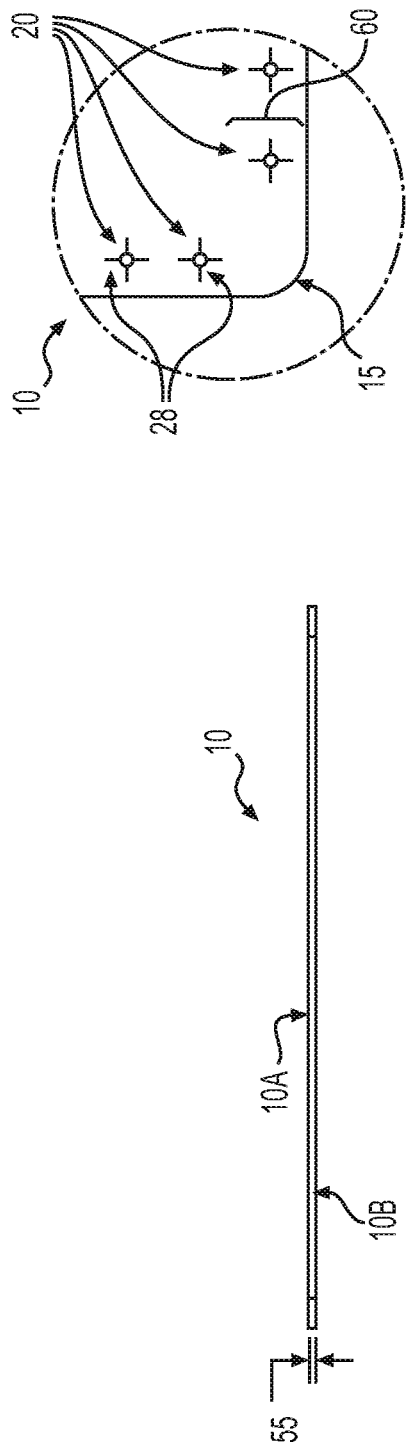

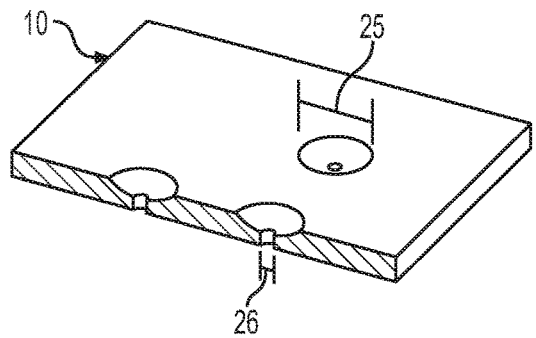
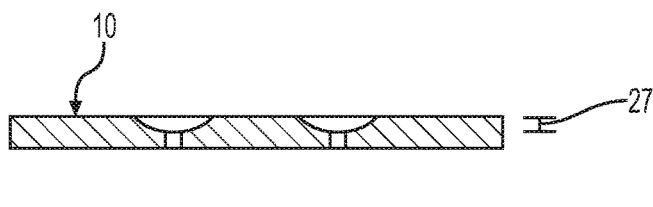
FIG. 2K  FIG. 2L
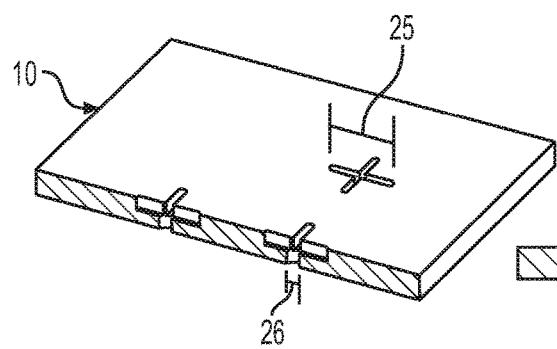
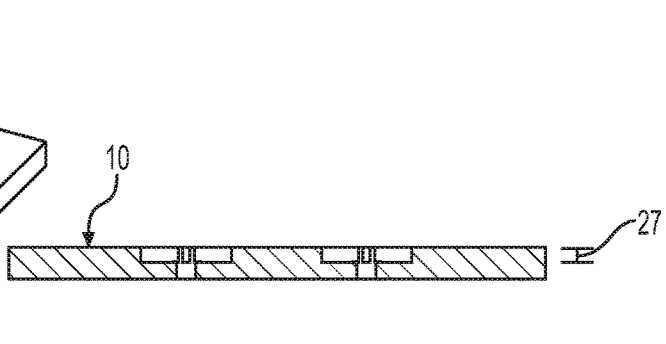
FIG. 2M  FIG. 2N
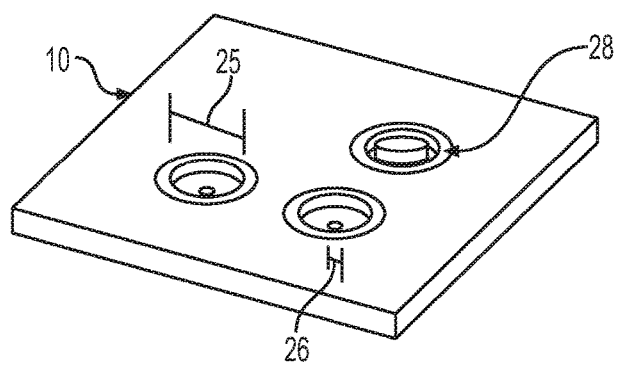
FIG. 2O

FIG. 3A

| TEST ORDER | TESTING GROUP | SPECIMEN NAME | THICKNESS (mm) | MAX LOAD (N) | COMMENT | NORMALIZED (N/mm) |
|---|---|---|---|---|---|---|
| 1 | LASER HOLE | HOLE 1 | 2.13 | 204.8 | END PULL OUT | 96.2 |
| 3 | LASER HOLE | HOLE 2 | 1.87 | 163.13 | ISTHMUS | 87.2 |
| 5 | LASER HOLE | HOLE 3 | 2.05 | 202.09 | ISTHMUS | 98.6 |
| 2 | LASER CONTROL | CONTROL 1 | 2.06 | 197.07 | END PULL OUT | 95.7 |
| 4 | LASER CONTROL | CONTROL 2 | 2 | 195.76 | ISTHMUS | 97.9 |
| 6 | LASER CONTROL | CONTROL 3 | 2.06 | 212.12 | ISTHMUS | 103.0 |
| 7 | BIOPSY CONTROL | CONTROL 4 | 1.46 | 144.29 | ISTHMUS | 98.8 |
| 9 | BIOPSY CONTROL | CONTROL 5 | 1.61 | 113.12 | END PULL OUT | 70.3 |
| 11 | BIOPSY CONTROL | CONTROL 6 | 1.89 | 129.41 | END PULL OUT | 68.5 |
| 8 | BIOPSY HOLE | BIOPSY 1 | 1.61 | 112.25 | END PULL OUT | 69.7 |
| 10 | BIOPSY HOLE | BIOPSY 2 | 1.68 | 111.37 | END PULL OUT | 66.3 |
| 12 | BIOPSY HOLE | BIOPSY 3 | 1.83 | 124.14 | END PULL OUT | 67.8 |

FIG. 3B

| SAMPLE GROUP | COMMENT | AVG THICKNESS | AVG ULT | AVG NORMALIZED | RATIO |
|---|---|---|---|---|---|
| CONTROL | - | 2.04 | 201.65 | 98.84 | 105% |
| TREATMENT1(HOLES) | LASER CUT HOLES 1.0-mm | 2.02 | 190.01 | 93.99 | |
| CONTROL | - | 1.65 | 128.94 | 79.19 | 117% |
| TREATMENT 2 (BIOPSY) | BIOPSY PUNCH 1-mm | 1.71 | 115.92 | 67.95 | |

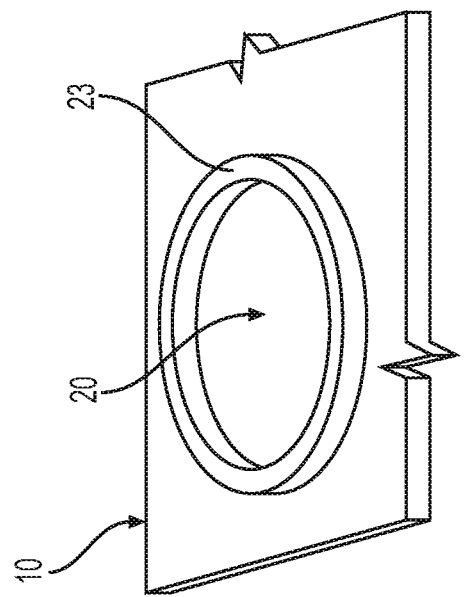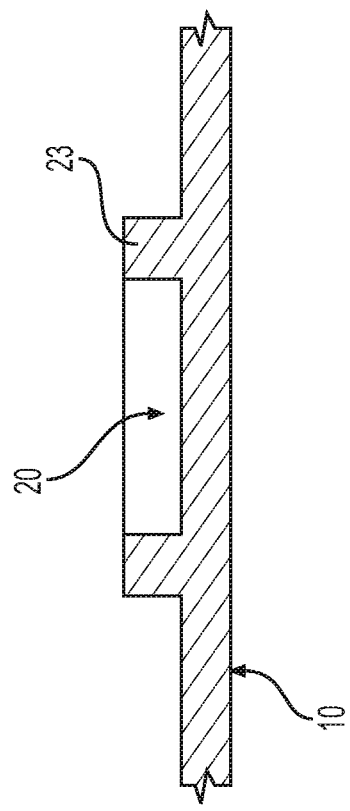

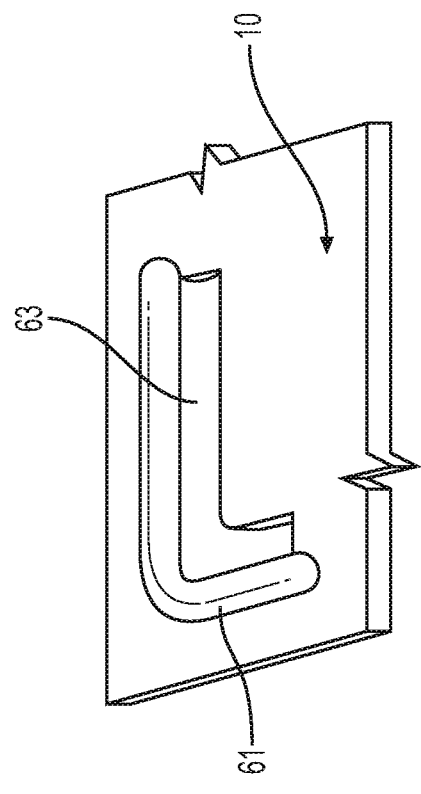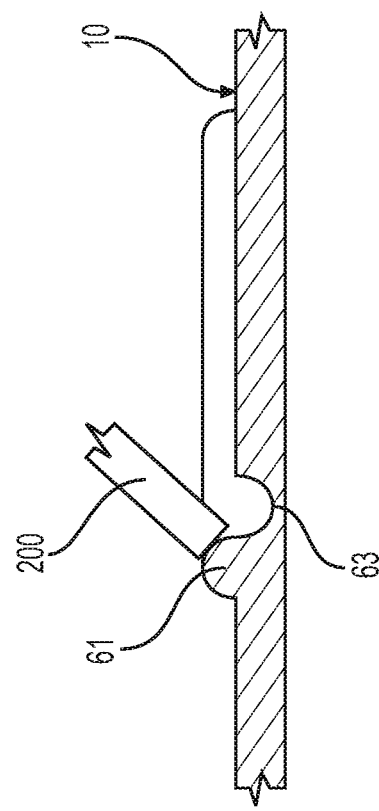

TISSUE MATRIX WITH PREFORMED OPENINGS OR PILOT OPENINGS

This application claims priority under 35 USC § 119 to U.S. Provisional Patent Application No. 62/404,815, filed Oct. 6, 2016, the entire contents of which is incorporated by reference in its entirety.

The present disclosure relates generally to acellular tissue matrix products, including tissue matrix products having openings at certain locations.

In many surgical operations, midline incisions are a widely used approach for access to the abdomen and involve cutting through the linea alba, a structure that connects the rectus abdominis muscles. Although a midline closure can heal, the resulting scar at the linea alba may be weaker than native tissue. Healing is made more challenging by the fact that the linea alba is an avascular structure. As a result, there is a high incidence of subsequent hernia formation at midline incision sites.

Surgeons currently use acellular tissue matrix products such as ALLODERM® and STRATTICE™, both dermal acellular matrices produced by LIFECELL® CORPORATION (Branchburg, N.J.), for treatment of a variety of different structural defects. For example, such products can be useful in abdominal wall repair (e.g., complex hernia repair), breast reconstruction, orthopedic surgery, and neurosurgical applications.

Such tissue matrix products are often provided as flexible sheets of material that can replace, augment, or alter existing tissues. For some applications, however, it may be desirable to include openings such as holes or perforations in the sheets, for example, to provide sites for securing surgical anchors such as sutures, clips, staples, or adhesives or to provide pathways to deliver an adhesive through the tissue matrix to adhere the tissue matrix to a host tissue.

Accordingly, the present application provides tissue matrix products having preformed openings such as holes or perforations. The openings may be provided in a configuration that provides the desired functionality without sacrificing other properties such as tensile strength and suture retention strength.

Similarly, some laparoscopic operations can use tissue matrix products to reinforce structures in the body. In laparoscopic operations, tackers are often used to fix the tissue matrix products to tissues to be treated. However, penetrating the tissue matrices can be challenging during laparoscopic surgery.

Thus, it may be desirable to remove material from the tissue matrix product at select locations to facilitate fixation using tacks or other devices. Openings such as pilot holes, divots, or thinned sections in the tissue matrix products, for example, can provide sites for securing surgical anchors such as sutures, clips, staples, or adhesive. Openings can also provide pathways to deliver an adhesive through the tissue matrix to adhere the tissue matrix to a host tissue.

Accordingly, the present application provides tissue matrix products having openings such as preformed pilot holes or divots. The openings may be provided in a configuration that provides the desired functionality without sacrificing other properties such as tensile strength and suture or tack retention strength.

Disclosed herein is a method of treatment. The method of treatment includes selecting an anatomical site for treatment and a tissue matrix product comprising a flexible sheet including a tissue matrix. The flexible sheet includes a group of openings passing through the tissue matrix in a perimeter region of the tissue matrix. The method of treatment also includes implanting the tissue matrix product in or on the anatomical site.

Disclosed herein is a method of treatment. The method of treatment includes selecting an anatomical site for treatment. The method of treatment also includes selecting a tissue matrix product comprising a flexible sheet including a tissue matrix. The flexible sheet includes a group of between 10 and 50 openings passing through the tissue matrix in a perimeter region of the tissue matrix. A portion of the group of openings lies on an outside line a first distance from an edge of the tissue matrix. A portion of the group of openings lies on an inside line a second distance from the edge of the tissue matrix. The flexible sheet has a rectangular shape having a width between 10 cm and 30 cm and a length between 10 cm and 30 cm. Each opening of the group of openings has a maximum dimension between about 0.5 mm and 2.0 mm. The distance between each opening of the group of openings and the edge of the flexible sheet is between 0.25 cm and 1.5 cm. The method of treatment further includes passing sutures through the openings of the portion of the group of openings on the inside line and through a portion of the anatomical site to close a wound or incision at the anatomical site. The method of treatment includes passing sutures through the openings of the portion of the group of openings on the outside line and through a portion of the anatomical site to secure the tissue matrix product to the anatomical site.

Disclosed herein is a device for use in a surgical procedure. The device comprises a tissue matrix product comprising a flexible sheet including a tissue matrix. The flexible sheet includes a group of openings passing through the tissue matrix in a perimeter region of the tissue matrix.

Disclosed herein is a method of treatment. The method of treatment includes selecting an anatomical site. The method of treatment further includes selecting a tissue matrix product comprising a flexible sheet including a tissue matrix. The flexible sheet includes a group of openings, each opening having a first portion passing partially through the tissue matrix. The method of treatment also includes implanting the tissue matrix product in or on the anatomical site.

Disclosed herein is a method of treatment. The method of treatment includes selecting an anatomical site for treatment. The method of treatment also includes selecting a tissue matrix product comprising a flexible sheet including a tissue matrix. The flexible sheet includes a first group of between 10 and 50 openings having a first portion passing partially through the tissue matrix in a perimeter region. A portion of the group of openings lies on an outside line and a portion of the group of openings lies on an inside line. The flexible sheet has a rectangular shape having a width between 10 cm and 30 cm and a length between 10 cm and 30 cm. Each opening of the group of openings has a maximum dimension between about 0.5 mm and 2.0 mm. The distance between each opening of the group of openings and an edge of the flexible sheet is between 0.25 cm and 1.5 cm. The method of treatment further includes implanting the tissue matrix product in or on the anatomical site.

Disclosed herein is a device for use in a surgical procedure. The device comprises a tissue matrix product comprising a flexible sheet including a tissue matrix. The flexible sheet includes a group of openings passing partially through the tissue matrix.

Also provided are methods of treatment including the disclosed products.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

FIG. 1A illustrates a top view of a tissue matrix product including openings, according to certain embodiments of the present disclosure.

FIG. 1B illustrates a side view of the tissue matrix product of FIG. 1A.

FIG. 1C illustrates an enlarged top view of a portion of the tissue matrix product of FIG. 1A.

FIGS. 2K-2L illustrate perspective sectional and cross-sectional views of a tissue matrix product including spherical countersunk pilot openings in accordance with various embodiments of the present disclosure.

FIGS. 2M-2N illustrate perspective sectional and cross-sectional views of a tissue matrix product including pilot openings with a cruciate shape in accordance with various embodiments of the present disclosure.

FIG. 2O illustrates a perspective view of a tissue matrix product including counterbored pilot openings and markings in accordance with various embodiments of the present disclosure.

FIG. 3A provides measurement data from suture retention testing of control samples of tissue matrix products and tissue matrix products produced according to certain embodiments of the present disclosure.

FIG. 3B provides averaged values of measurement data and comparison data for control samples and tissue matrix products according to certain embodiments of the present disclosure.

FIG. 10A depicts a perspective view of a portion of a tissue matrix product having a raised portion surrounding an opening in accordance with embodiments of the present disclosure.

FIG. 10B depicts a side view of the portion of tissue matrix product of FIG. 10A.

FIG. 11A depicts a perspective view of a portion of a tissue matrix product having a ridge and a trough in accordance with embodiments of the present disclosure.

FIG. 11B depicts a side view of the portion of tissue matrix product shown in FIG. 11A during a fixation procedure in accordance with embodiments of the present disclosure.

DESCRIPTION OF EXEMPLARY EMBODIMENTS

Figure 2A:
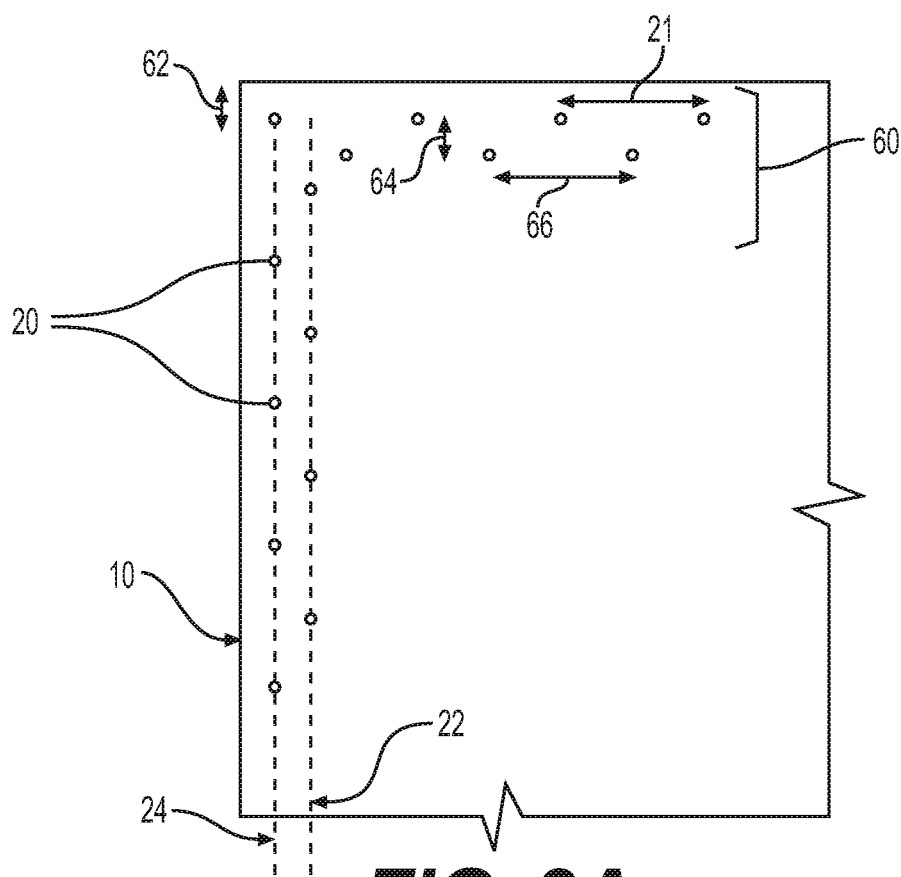
FIGS. 2A-2D illustrate top views of portions of a tissue matrix product having different patterns of openings such as pilot openings or divots according to certain embodiments of the present disclosure.
Figure 2B:
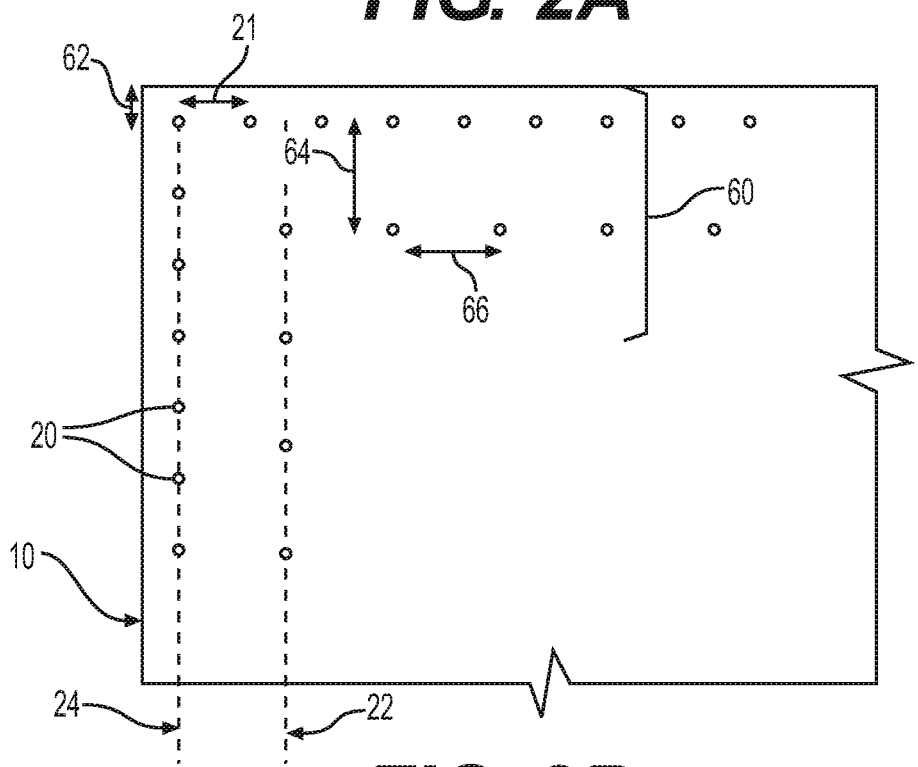
Figure 2C:
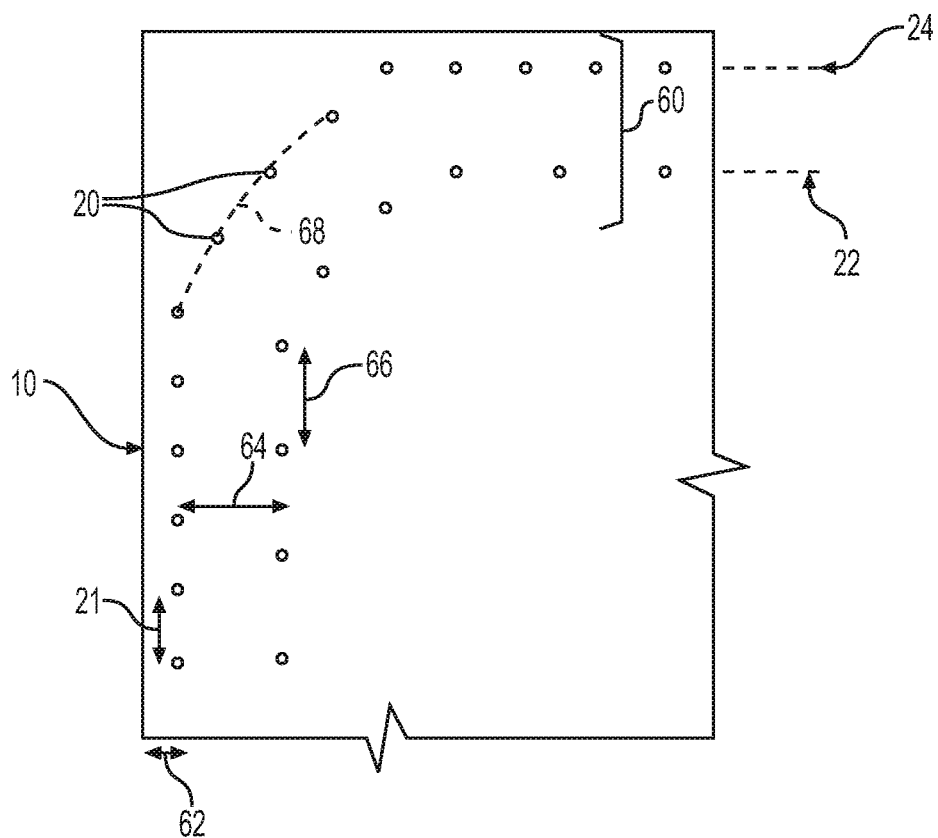
Figure 2D:
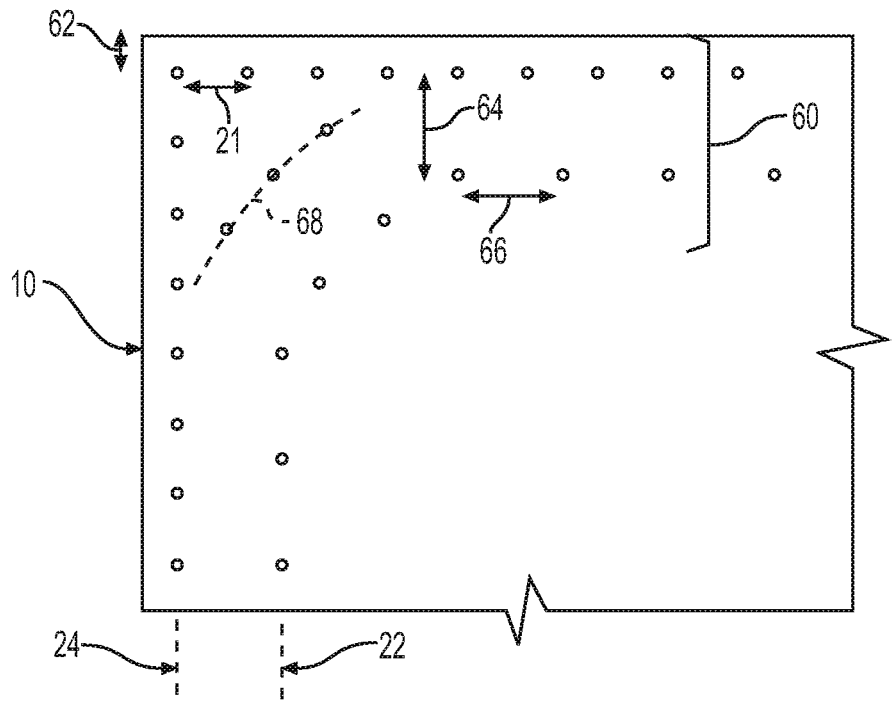

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including" as well as other forms, such as "includes" and "included," is not limiting. Any range described herein will be understood to include the endpoints and all values between the endpoints.

As used herein, "openings" is generally used to refer to any opening that passes at least partially through a flexible sheet of material and can refer to holes, perforations, pilot holes, divots, countersinks, counterbores, or thinned sections of the device.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure relates generally to devices for surgical procedures and systems and methods relating to such devices. The devices can be used for tissue augmentation, repair or regeneration of damaged tissue, and/or correction of tissue defects. As such, the devices and methods discussed herein can be suitable for a wide range of surgical applications such as, for example, abdominal wall treatment or repair, prophylactic treatment of post-operative complications (e.g., to prevent hernia, dehiscence, or other post-operative abdominal complications), and hernia treatment (e.g., any abdominal or visceral hernia, such as a hiatal hernia, inguinal hernia, parastomal hernia, or midline abdominal hernia). The devices disclosed herein can also be used to treat other tissue sites, including, for example, a pelvic floor, breasts, or connective tissue (tendons, ligaments, or fascia), or to assist in structural defect correction or prevention. The devices disclosed herein can be compatible with laparoscopic techniques or with open procedures.

The devices and associated methods discussed herein can include a flexible sheet of biologic material, such as an acellular tissue matrix. Such tissue matrix materials are used for a variety of surgical applications and have become an important tool for treating or preventing many problems associated with trauma, post-operative complications, and/or structural defects due to aging, disease, congenital or acquired defects, or iatrogenic problems.

The incidence of hernia formation at the site of a healed midline incision is high. Studies have indicated that separation of the closure of a midline incision in the early timeframe may predict subsequent formation of a hernia. As such, it may be important to minimize separation of the primary closure. In some cases, this could be achieved using a surgical material to reinforce the primary closure.

Closure of a laparotomy incision often occurs as the last step in a long surgical procedure. In some cases, the surgical procedure may have lasted for several hours or more and, thus, an important goal is minimization of the time and effort needed to implant a surgical material. Systems and methods of the present disclosure can help to reduce the time that a surgeon spends implanting a surgical material such as a mesh or matrix product.

For some surgical procedures, it may be desirable to include openings in the tissue matrix. Properly designed openings can be useful for securing the tissue matrices within a surgical site. For example, some tissue matrix materials are designed to be strong and potentially relatively thick. Accordingly, fixation of such devices to surrounding tissues using conventional devices such as sutures, staples, or clips, can sometimes be challenging and/or time consuming. In addition, a potential danger exists when a surgeon is suturing with excessive force to penetrate strong matrix materials in that the surgeon may overshoot if the suture needle or tack unexpectedly passes through the tissue matrix. This event can lead to unintended needle sticks of the surgeon or patient. Further, excessive force applied to the tissue matrix product to pass a suture needle or tack through the matrix can lead to inadvertent damage to the tissue matrix. Therefore, tissue matrices with preformed openings or pilot openings that can be affixed using sutures, tacks, or other means are desirable.

Preformed openings or pilot openings in tissue matrices can provide other advantages as well, including easing or improving laparoscopic surgeries. When a tacking instrument or other device (sutures, surgical staples, or clips) is used to fixate the tissue matrix, preformed openings or pilot openings can be designed to have improved fixation or ease of use for a specific fixation instrument design. In addition, due to surgeons' lack of the tools or processes to create optimal opening configurations, the preformed openings or pilot openings can be better suited for a particular fixation device than openings generated intra-operatively. Furthermore, in cases where a surgeon has limited mobility or space, such as during placement of a tissue matrix in a retro-muscular position to reinforce a laparotomy closure or in laparoscopic procedures, the preformed openings can make implantation faster and easier. In some cases, the preformed openings or pilot openings can have a dimension smaller than the diameter of the tack or suture. In some cases, preformed divots may not penetrate completely through the tissue matrix. The pilot opening or divot can operate as a guide to help land a needle, punch, or tack to prevent movement while inserting the needle, punch, or tack through the tissue matrix.

On the other hand, openings in tissue matrices should be configured to prevent unacceptable changes in other materials properties. For example, the openings in a flexible sheet of tissue matrix can be sized, shaped, and positioned such that the tissue matrix does not experience an unacceptable degradation in important mechanical properties such as tensile strength, elasticity, burst strength, and/or suture retention strength. Accordingly, the present application provides improved tissue matrix products that include a group of openings that may provide the aforementioned advantages without causing unacceptable alterations in other material properties.

According to certain embodiments, the present application provides tissue products for use in surgical procedures. The tissue products can include a flexible sheet 10 (FIGS. 1A-1C) comprising a tissue matrix, wherein the flexible sheet includes one or more openings 20 passing through the tissue matrix 10. The openings 20 can be sized and positioned on the flexible sheet of tissue matrix 10 to maintain a desired tensile strength of the sheet, as compared to a sheet without the openings 20.

Figure 4:
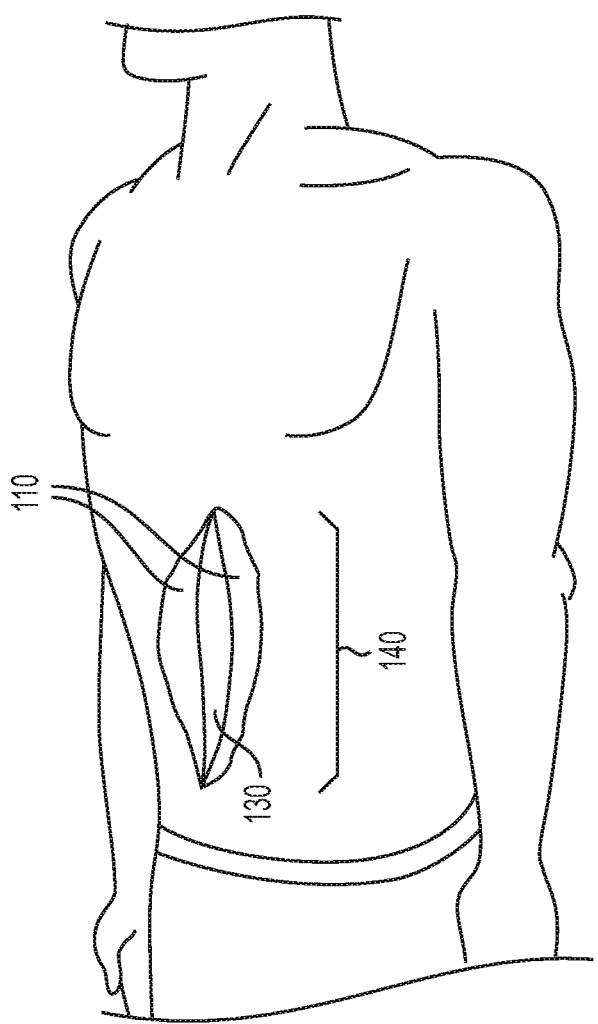
FIG. 4 depicts an abdominal surgical site that may be treated with a tissue matrix product in accordance with certain embodiments of the present disclosure.
Figure 5:
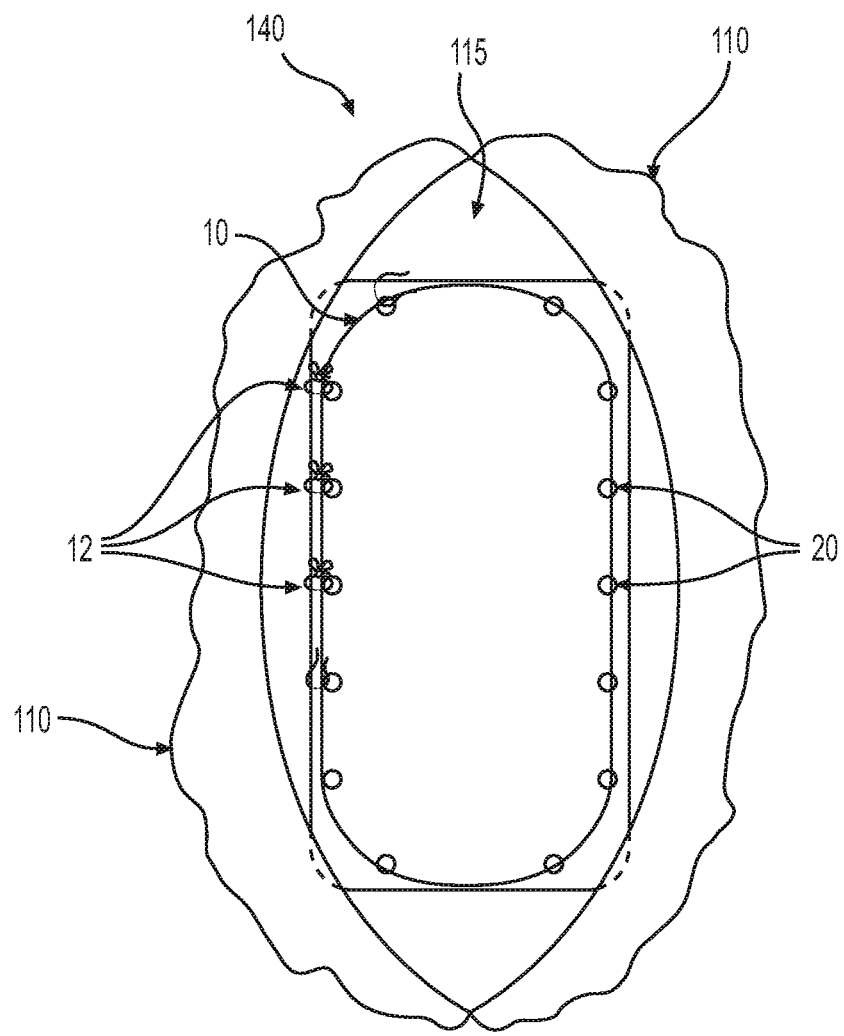
FIG. 5 illustrates an abdominal opening treated using tissue matrix products of the present disclosure.

The devices disclosed herein can be used for treating a variety of different anatomical sites. For example, FIGS. 4 and 5 illustrate methods of treatment of an abdominal wall or abdominal opening using tissue matrix products 10 of the present application. The methods of treatment are described in more detail below; in general, the device 10 can be used to treat portions of the abdominal wall 150, or other anatomical sites, while using one or more openings 20 to provide a site for fixation using sutures or other fixation means. Furthermore, as discussed below, the devices 10 can be implanted at a variety of different locations to support various anatomical structures and/or treat a variety of different conditions.

FIGS. 1A-1C illustrate different views of an exemplary tissue matrix product 10 including openings 20. The tissue matrix product 10 can include a flexible sheet of material having a length 40, a width 50, and a thickness 55. The length 40, width 50, and thickness 55 can be selected based on the desired surgical indication, e.g., to provide a sufficient surface area (measured in terms of the length 40 and width 50) and structural stability (e.g., based on strength, tensile properties, suture retention, burst strength, etc.). For dermal tissue matrix materials, the thickness 55 can vary, but may be between, for example, 0.75 mm to 4 mm, 0.75 mm to 1.25 mm, or 1.05 mm to 1.55 mm. In some embodiments, the width 50 of the flexible sheet can be between 4 cm and 50 cm. In some embodiments, the length 40 of the flexible sheet can be between 4 cm and 50 cm. In some embodiments, the thickness 55 of the tissue matrix product 10 is small enough that the tissue matrix product 10 can easily be rolled or folded to fit through a laparoscopic trocar or cannula for insertion into a patient through a laparoscopic opening. In some embodiments, the openings 20 can be holes, pilot holes, divots, or thinned sections as described in detail below.

The tissue matrices used to produce the products 10 described herein can include a variety of different materials. For example, an acellular tissue matrix or other tissue product can be selected to allow tissue ingrowth and remodeling to assist in regeneration of tissue normally found at the site where the matrix is implanted. For example, an acellular tissue matrix, when implanted on or into subdermal tissue, fascia, mammary tissue, or other tissue, may be selected to allow regeneration of the tissue without excessive fibrosis or scar formation. In certain embodiments, the devices can be formed from ALLODERM® or STRATTICE™ (LIFECELL® CORPORATION, BRANCHBURG, N.J.) which are human and porcine acellular dermal matrices, respectively. Alternatively, other suitable acellular tissue matrices can be used. For example, a number of biological scaffold materials as described in Badylak et al., "Extracellular Matrix as a Biological Scaffold Material: Structure and Function," *Acta Biomaterialia* (2008), doi:10.1016/j.actbio.2008.09.013, or any other similar materials, can be used. The devices described herein can be produced from a variety of different human or animal tissues including human, porcine, ovine, bovine, or other animal tissues.

As stated above, the products 10 can include one or more openings 20 that can be sized and positioned to provide one or more desired properties. As illustrated in FIG. 1A, the product 10 includes a total of thirty-two holes, but a range in the number of holes can be used. Further, as shown in FIG. 1A, the openings 20 can be positioned within a perimeter region 60 of the product 10. The perimeter region 60 can be sized to allow an area for passage of sutures or other connection devices. In various embodiments, the perimeter region 60 may extend inward from an edge of the product 10 by about 0.5 cm, 0.25 cm-0.75 cm, 0.25 cm-2.0 cm, or values in between. Larger or smaller perimeter regions 60 can be used. In various embodiments, the openings 20 can be placed with each opening 20 about the same distance 62 from the edge of the tissue product or with different distances 62 from the edge of the tissue product for each opening 20.

As shown in FIGS. 2A-2D, the openings 20 can be arranged in patterns within the perimeter region 60. For example, the openings 20 can be arranged in a "double-crown" pattern in which a plurality of openings 20 on an inside line 22 are interspersed within a plurality of openings 20 on an outside line 24 as shown in FIG. 2A. In some embodiments, openings 20 on both the inside line 22 and outside line 24 can be used to fixate the device 10 to the tissue. Providing additional fixation openings may provide better apposition of the tissue matrix to the tissue and can spread the stress over a larger area to make the device 10 less susceptible to tearing. In some embodiments, the openings 20 on the inside line 22 and outside line 24 can serve different purposes as discussed in greater detail below with respect to FIG. 6. In some embodiments, the distance 64 between the inside line 22 and the outside line 24 can be chosen to maintain strength (e.g., tensile strength, burst strength, or suture retention strength) or other properties while reducing the risk of undesirable behavior such as suture pull-through. In some embodiments, the inside line 22 or outside line 24 can have an arc 68 (FIGS. 2C and 2D) or other non-linear configuration.

In some embodiments, the openings 20 can be spaced apart from one another by a distance 21, 66 chosen to provide enough openings 20 on the product 10 to secure the tissue matrix sheet without compromising mechanical properties of the product 10. In exemplary embodiments, the distance 21, 66 between openings 20 is about 1.5 cm, 1.0 cm-2.0 cm, 0.5 cm-2.5 cm, or values in between. In some embodiments, the distance 21 between openings 20 on the outside line 24 can be different than the distance 66 between openings 20 on the inside line 22.

The products 10 described herein can have a variety of shapes and sizes. For example, each of the flexible sheets of tissue matrix illustrated in FIGS. 1A-1C and FIGS. 2A-2D are rectangular, which may be used in abdominal wall procedures or other procedures. Furthermore, a rectangular shape can be trimmed or reshaped based on a specific patient's needs or surgeon's preferences. It will be appreciated, however, that other shapes can be used, includes circular, oval, square, triangular, bi-convex, or asymmetric shapes. In some embodiments, the sheet can have rounded corners 15 (FIG. 1C). When a sheet has square corners, the corners may fold after implantation. As a result, the folded corner may not have good apposition to the host tissue, and the folded portion may not incorporate into the host tissue. The use of rounded corners 15 can improve apposition to the host tissue and can prevent small void spaces or portions of unincorporated tissue matrix. In some embodiments such as that shown in FIG. 2D, openings 20 can be provided at the corners of the device 10 such that openings 20 are always maintained near the edge of the device 10 whether it is used as a rectangular piece or trimmed to have rounded corners 15.

In some embodiments, openings 20 can be straight-walled holes as depicted above with reference to FIGS. 1A-2D. For certain surgical procedures involving, for example, suturing, straight-walled holes may be suitable. However, the openings 20 can have a variety of shapes and sizes other than straight-walled holes as described below with reference to FIGS. 2E-2O. For certain surgical procedures involving, for example, tacking, shapes other than straight-walled holes may provide advantages.

The size and shape of each of the openings 20 can be varied. Generally, however, the openings 20 are sized and shaped to preserve the mechanical properties of the sheet of tissue matrix 10, while allowing passage of sutures or other anchors through the openings. In accordance with various embodiments, the openings 20 can have a first diameter or inner dimension 25 at a top tissue sheet surface 10A and a second diameter or inner dimension 26 at a bottom tissue sheet surface 10B. In some embodiments, the first diameter or inner dimension 25 is greater than the second diameter or inner dimension 26. In some embodiments, the first diameter or inner dimension 25 can be the same as the second diameter or inner dimension 26. As an example, the openings can be sized such that they have the first diameter 25 or the second diameter 26 of about 1.0 mm, between about 0.5 mm and 2.0 mm, or any values within the aforementioned range(s). In some embodiments, the first diameter or inner dimension 25 of the openings 20 can be large enough that the openings 20 are easily seen using a laparoscopic camera or by visual inspection. In some embodiments, the second diameter or inner dimension 26 of the openings 20 can be large enough to reduce resistance for an anchor (e.g., suture, tack, or clip) to pass through yet small enough that sufficient material remains for the anchor to form a mechanical engagement without passing completely through the sheet. The openings 20 can have a depth 27 at which point the first diameter 25 transitions to the second diameter 26. The transition can be gradual or abrupt and can be continuous or discontinuous. In some embodiments, the first diameter or inner dimension 25 of the openings 20 can be chosen to be larger than the largest dimension of a tack 35 to be used. In these embodiments, the tack 35 can pass deep enough into the tissue matrix product 10 that the top of the tack 35 is below the tissue sheet surface 10A.

Figure 2E:
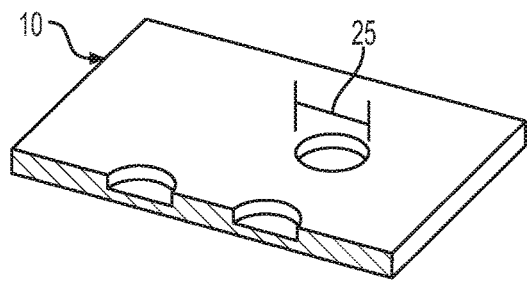
FIGS. 2E-2F illustrate perspective sectional and cross-sectional views of a tissue matrix product including divots in accordance with various embodiments of the present disclosure.
Figure 2F:
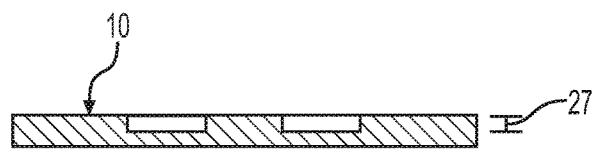

As shown in FIGS. 2E and 2F, the openings 20 can be divots that have a second diameter 26 of zero and a depth 27 less than the full thickness of the tissue matrix 10'. The depth 27 of the divots can be chosen as needed to sufficiently reduce the penetration force encountered when attempting to pass a needle or tack through the tissue matrix 10'. In some embodiments, the depth 27 of the opening 20 can be 25%, 50%, 75%, 90%, or any suitable percentage of the thickness 55 of the tissue matrix 10'. Openings 20 that are divots can provide better retention for some multi-pronged tacks or staples than through holes because additional material remains for the tack or staple to "grab."

Figure 2G:
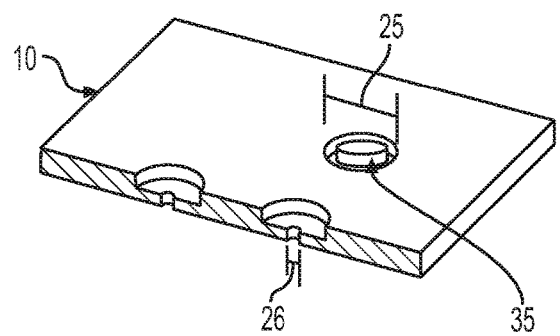
FIGS. 2G-2H illustrate perspective sectional and cross-sectional views of a tissue matrix product including counterbored pilot openings in accordance with various embodiments of the present disclosure.
Figure 2H:
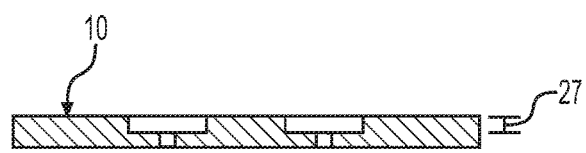
Figure 2I:
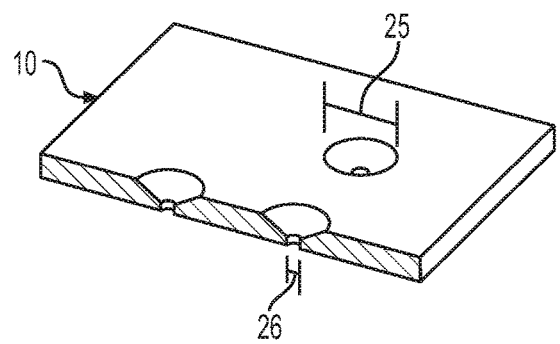
FIGS. 2I-2J illustrate perspective sectional and cross-sectional views of a tissue matrix product including conical countersunk pilot openings in accordance with various embodiments of the present disclosure.
Figure 2J:

FIGS. 2G-2N illustrate example tissue matrices 10' having pilot openings 20 in a variety of shapes. As shown in FIGS. 2G and 2H, the pilot openings 20 can have a counterbored shape with straight sidewalls. In some embodiments, the pilot openings 20 can have a cross-section that varies along the thickness of the tissue sheet such as, for example, a cone or frustum shape. As shown in FIGS. 2I and 2J, the pilot openings 20 can have a countersunk shape with sidewalls that narrow linearly from the first diameter 25 to the second diameter 26. The pilot openings 20 can also have a countersunk shape with sidewalls that narrow from the first diameter 25 to the second diameter 26 along a non-linear path such as a polynomial or discontinuous path. As shown in FIGS. 2K and 2L, the pilot openings 20 can have sidewalls that are spherical or quadratic. In some embodiments, countersunk pilot openings 20 can help improve fixation when anchors or tacks enter the tissue matrix 10' at a non-normal entry angle (i.e., an angle different from 90°). In these embodiments, the countersunk openings can help align the tack 35 with respect to the tissue matrix 10' and allow the tack to penetrate deeper into the tissue matrix 10' before encountering mechanical resistance due to the tack head hitting the top surface 10A of the tissue matrix 10'.

In some embodiments, the openings 20 can have a polygonal cross-sectional shape with three or more sides, or can include irregular curved shapes. The openings 20 can have a circular or square cross-section or can have a shape with an aspect ratio other than 1:1 including oval or diamond shapes. As shown in FIGS. 2M and 2N, the openings 20 can have a cross or cruciate design to allow penetration of tacks through the tissue matrix 10' while leaving a sufficient amount of sheet material for the fixation modality (e.g., tacks, sutures, or adhesive) to grasp. A similar advantage may be found with openings 20 that have slit or star-shaped cross sections. In some embodiments, the openings 20 can have a cross-section that varies along the thickness of the tissue sheet such as, for example, a cone or frustum shape. In some embodiments, the opening 20 may be cut in a helical or thread-like manner to enhance penetration and holding of screw-type tacks.

The trajectory of each opening 20 through the tissue sheet can be cylindrical and normal to the tissue sheet surface 10A, 10B. In some embodiments, the trajectory of each opening 20 can be non-normal to the surface 10A, 10B of the tissue matrix sheet and can be, for example, slanted or angled with respect to the surface 10A, 10B of the tissue matrix sheet. In some embodiments, the trajectory of the opening 20 can be non-linear including paths with curved or polynomial properties. In some embodiments, the opening 20 can contain two or more trajectories.

The openings 20 can be shaped to maintain sheet mechanical properties. For example, to prevent excessive force due to tensile forces of sutures passed through an opening 20 or high stress points, each opening can have a rounded border (e.g., oval, circular, rounded but asymmetric). In some embodiments, areas of the tissue matrix sheet surrounding or next to the openings 20 can be reinforced to increase the retention strength. The sheet may be reinforced by, for example, cross-linking constituents of the tissue matrix, compressing the tissue matrix to increase the density for the entire tissue matrix or a portion of the tissue matrix, adding material to an area to increase the local mass, increasing the material thickness, or any other suitable method. In some embodiments, the thickness 55 of the tissue matrix sheet can be modified at different points to provide advantageous results. For example, unmodified regions of thickness 55 may provide greater fixation retention strength (e.g., at the location of sutures) while removal of material to reduce thickness 55 of the tissue matrix sheet can allow the use of tacks.

Markings 28 can be used to help identify the location of one or more openings 20. In some embodiments, the markings 28 can be, for example, a line or symbol in close proximity to the opening 20 including an arrow, hash mark, or any other suitable visual or tactile indicator. In some embodiments, the markings 28 can be, for example, a line or symbol surrounding the opening 20 including a circumscribed circle (as shown in FIG. 2O), cross-hairs (as shown in FIG. 1C), or any other suitable visual or tactile indicator.

The markings 28 can be made using a variety of techniques including, but not limited to, ink markings, deposited material markings, laser engraved markings, raised or depressed features, or any other suitable method. In some embodiments, the ink markings can have a fluorescent feature to enhance visibility. In some embodiments, the deposited material markings can include a metal or metallic gloss to increase reflectivity and enhance visibility.

The openings 20 can be formed in a variety of ways. For example, in one embodiment, the openings are produced using a machine press with a cutting die including elongated sharpened extensions. The sharpened extensions can be placed in a desired pattern to cut or puncture openings 20 while also including a knife or cutting die to cut the perimeter of the device 10. Alternatively the openings 20 can be cut individually, by hand or using suitable cutting tools. In some embodiments, the openings 20 can be created using a biopsy punch or can be created using laser cutting or ablation. In some embodiments, openings 20 including divots can be created using cryomachining methods. In some embodiments, openings 20 can be machined into the tissue in a wet, dry, or frozen state using traditional machining methods including end mills, drill mills, drills, fly cutters, or other rotary cutting tools.

The size and shape of the openings as well as other sheet properties (e.g., thickness) can be configured to provide openings that will maintain suture retention strength if sutures or other fixation devices are passed through an opening. For example, the suture retention strength of each opening 20 can be configured such that it is at least 60%, at least 70%, at least 80%, at least 90%, at least 95%, at least 99%, or approximately 100% of the suture retention strength of a region of the same tissue matrix without an opening 20.

Suture retention can be measured using a simple technique. Specifically, a suture or suture analog (e.g., a steel wire) can be passed through the tissue to form a loop and tension can be applied until the material tears. The amount of force (in newtons) needed to tear the tissue is the suture retention strength. The suture retention strength can be measured by passing the suture through one of the openings 20 to measure the suture retention when an opening is used.

The suture retention strength of tissue sheets having openings in accordance with the present invention was measured in relation to standard tissue sheets. The results of the measurements are shown in the tables in FIGS. 3A and 3B. The openings were created either by biopsy punch or by laser cut and were cut all the way through the tissue. As shown in the table, the comparison includes three samples with laser cut openings, three samples with biopsy punched openings, and six control samples. A suture was passed through an opening in each test sample and tied off to itself to create a loop. The suture loop was hung on a hook and the sample was clamped below the suture to prevent movement. The hook was displaced at a constant rate and the load applied to each suture was measured. The measured suture retention strength is the maximum load or force measured before an adverse event occurred. Adverse events included pull out of the suture end from the tissue or channeling of the suture through the tissue to an end or an adjacent opening (isthmus). To control for differences in tissue thickness, each force measurement result was normalized to the thickness of the tissue, and the data within each sample condition was then averaged. The difference in normalized force that was sustained by control samples and samples with openings created by laser cut and biopsy punch was only 5% and 17%, respectively.

The specific number of openings 20 in the devices 10 illustrated can be varied. For example, a sheet can include between 10 and 80 openings, between 20 and 40 openings, between 20 and 50 openings, between 10 and 30 openings, between 14 and 64 openings, up to 120 openings or other values in between. Further, the sheets can have a width 50 between 10 cm and 50 cm, between 10 cm and 25 cm, between 20 cm and 25 cm, or any ranges in between. In addition the devices 10 can have a length 40 between 10 cm and 50 cm, between 15 cm and 30 cm, or between 20 cm and 25 cm.

The products described herein are generally described with reference to acellular tissue matrices, but it will be appreciated that the tissue matrices can be pre-treated with exogenous cells or other therapeutic components prior to or after implantation. Accordingly, the devices can include tissue matrix products from which substantially all native cellular material has been removed, but which include exogenous cellular sources such as stem cells, fibroblasts, platelets, blood cells, or other cell sources.

The devices described herein can be used in a variety of different surgical operations, including during operations that require production of large abdominal incisions or include treatment of abdominal wall defects. An example of a midline abdominal defect, which can include an incision, is illustrated in FIG. 4. As shown, the incision 140 can include incision margins 110 that are retracted to expose a surgical site 130. Such midline abdominal incisions are commonly formed for open surgical procedures. But, as noted below, the devices 10 of the present disclosure can assist in closure of a midline incision or can be used to assist in closure of other incisions (e.g., laterally positioned incisions, transverse incisions, or oblique incisions).

For example, FIG. 5 illustrates an abdominal opening treated using tissue matrix products of the present disclosure. As shown, the device 10 can be implanted at an anatomical site 140. In some embodiments, the anatomical site 140 can be an incision. The anatomical site can include incision margins 110 and abdominal fascial layers 115. In accordance with various embodiments, the device 10 can overlap the abdominal fascial layers 115 by 3 to 5 cm. In some embodiments, the device 10 can be placed under the skin of a patient and secured to the patient's anatomy such as, e.g., the fascia 115. For example, sutures 12 can be passed through the openings 20 of the device 10 and through the fascia 115 before being tied. Similarly, the device can be tacked or adhered to the appropriate tissue through the openings 20. After the device 10 is implanted at the anatomical site, the incision can be finally closed.

Figure 6:
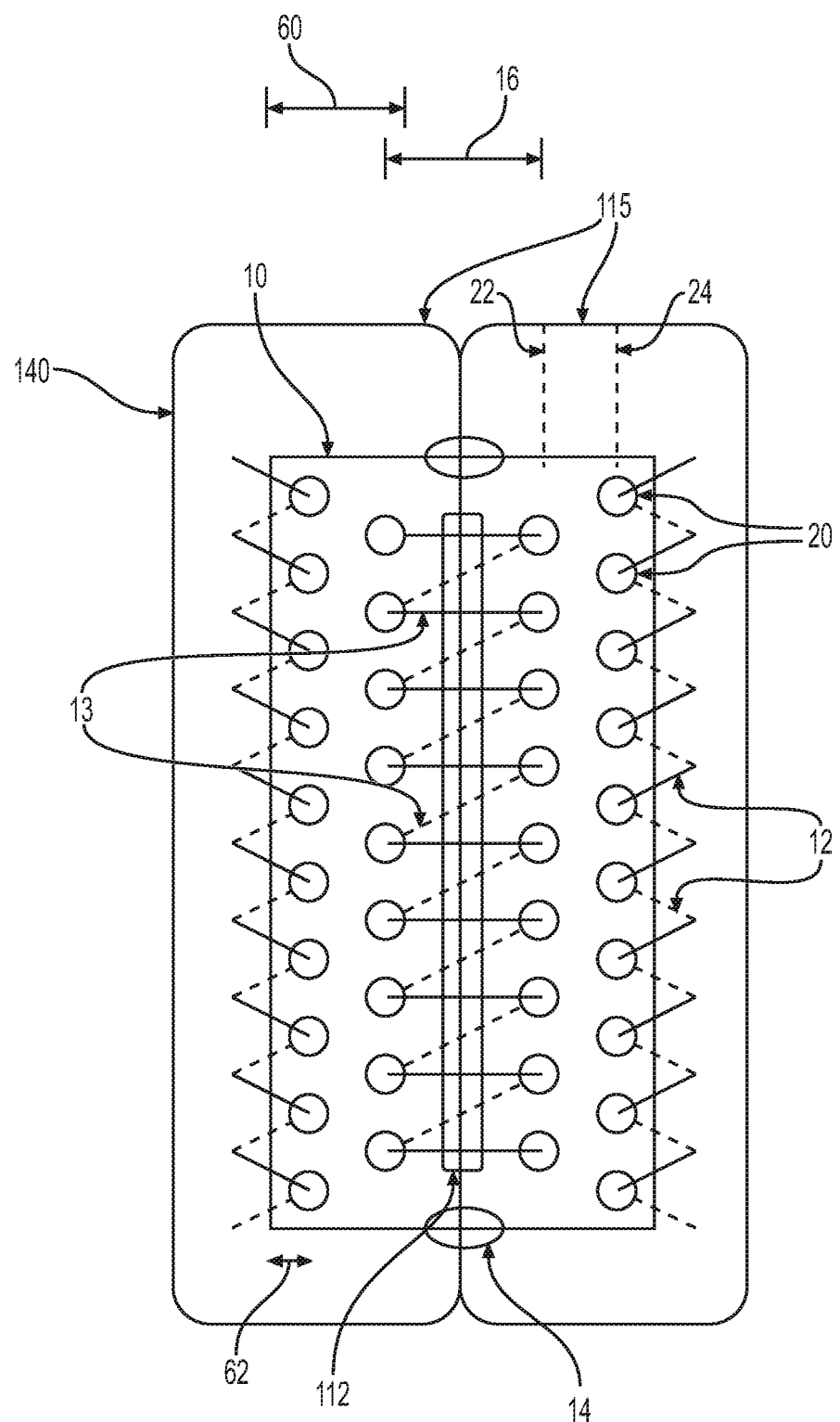
FIG. 6 depicts an abdominal wall treated using tissue matrix products of the present disclosure.

FIG. 6 illustrates an abdominal wall treated using tissue matrix products of the present disclosure. As shown, the device 10 can be implanted at an anatomical site 140. In some embodiments, the anatomical site 140 can be an incision. The anatomical site can include abdominal fascial layers 115. The device 10 can include openings 20 on an inside line 22 for primary closure and on an outside line 24 for perimeter fixation. The device 10 can be placed over a wound/incision closure at the anatomical site 140 to provide structural reinforcement.

In some embodiments, the openings 20 on the primary closure line 22 can facilitate suturing of a midline incision. The risk of incisional hernia formation after suture closure of a laparotomy incision can be reduced by using sutures with a small bite (e.g., 5 mm) and small spaces between bites (e.g., 5 mm). For a running suture, this guidance results in a ratio of at least 4:1 between suture length and wound (i.e., incision) length. In some embodiments, the openings 20 on the primary closure line 22 can be positioned to match a desired ratio of suture length to wound length such as 3:1, 4:1, 5:1, or any suitable ratio. The placement of the openings 20 on the primary closure line 22 can allow the surgeon to easily place the suture at the appropriate spacing while also including the device 10 into the running stitch. As a result, the device 10 can act as a pledget to help prevent suture pull-through of the linea alba and can offload local stresses at the incision from the tissue to the device 10.

In accordance with various embodiments, the method of treatment can include placing a suture through the openings 20 on the primary closure line or inside line 22 of the device 10 and through two sides of an opening (e.g., an abdominal opening) to bring the two sides into apposition. A continuous running suture can be used or multiple sutures can be used. The sutures can pass through portions of the anatomical site to close a wound or incision at the anatomical site. In some embodiments, the sutures can include mattress stitches 14, simple interrupted stitches, simple continuous (i.e., "baseball") stitches 13, or any other style or pattern of stitches as appropriate for a particular application. The method can also include placing fixation sutures 12 through openings 20 on the perimeter fixation line or outside line 24 to retain the device 10 in position relative to the abdominal fascial layers 115.

In accordance with various embodiments, the openings 20 can be positioned within a perimeter region 60 of the device 10. The perimeter region 60 can be sized to allow an area for passage of sutures or other connection devices. In various embodiments, the perimeter region 60 may extend inward from an edge of the product 10 by about 0.5 cm, 0.25 cm-0.75 cm, 0.25 cm-2.0 cm, or values in between. Larger or smaller perimeter regions 60 can be used. In various embodiments, the openings 20 on the perimeter fixation line 24 can be placed with each opening 20 about the same distance 62 from the edge of the tissue product or with different distances 62 from the edge of the tissue product for each opening 20. In various embodiments, the openings 20 on the primary closure line 22 can be placed with each opening 20 about the same distance from the edge of the tissue product or with different distances from the edge of the tissue product for each opening 20. The openings 20 on the primary closure line 22 and the perimeter fixation line 24 can be arranged in various patterns such as a "double crown" pattern. In some embodiments, the pattern can be chosen to minimize stress on the device 10 or reduce the potential for suture pull-through or isthmus to an adjacent opening. In various embodiments, openings on the primary closure line 22 and the perimeter fixation line 24 can have properties similar to the openings described above with reference to FIGS. 1A-2O. In some embodiments, the spacing 16 between openings 20 on one primary closure line and the opposite primary closure line 22 can be in the range from 0.5-3 mm. In one embodiment, the spacing 16 between opposing primary closure lines 22 can be 1 mm.

Figure 7:
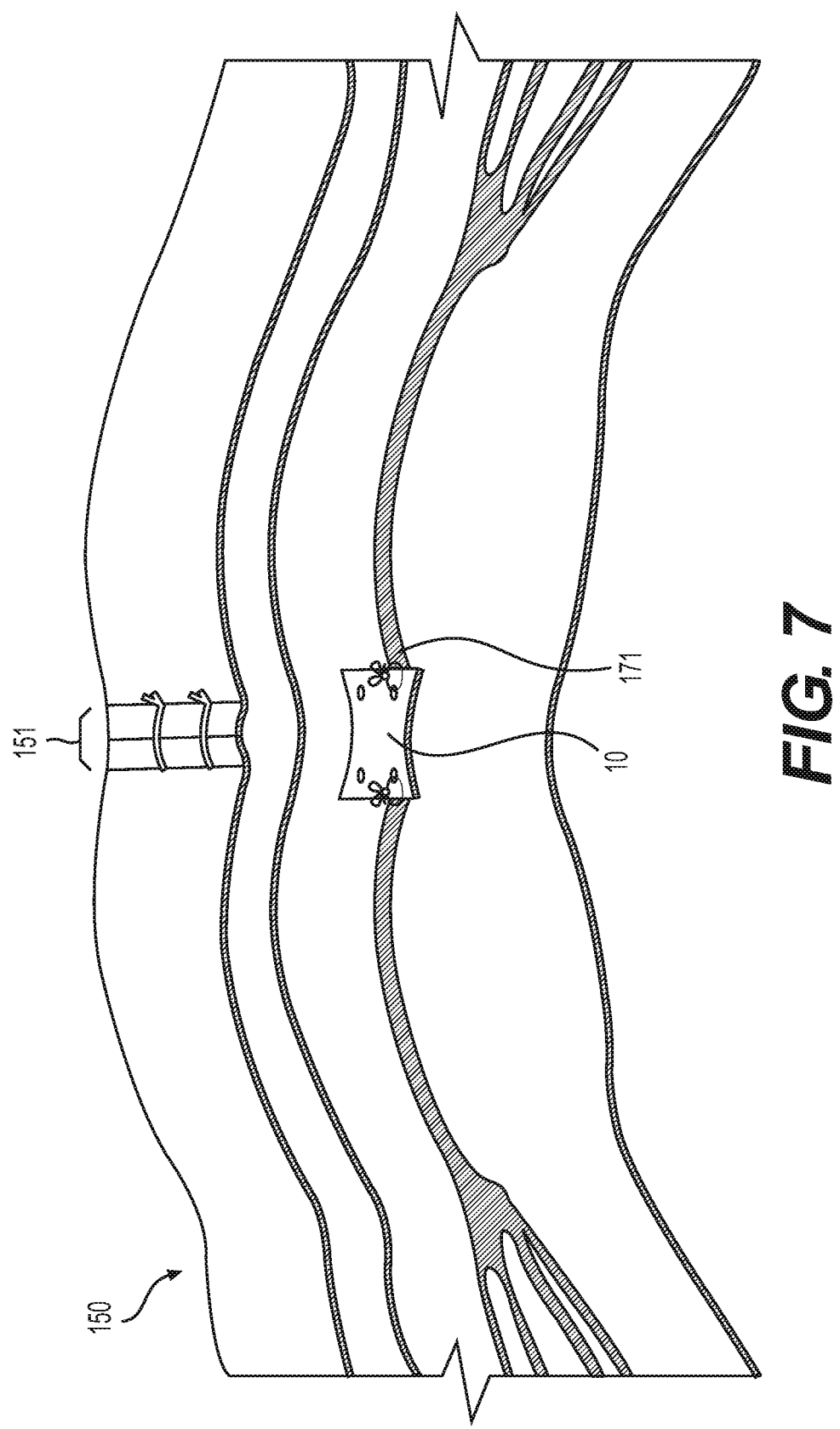
FIG. 7 illustrates layers of an abdominal wall that may be treated using tissue matrix products in accordance with the present disclosure.

FIG. 7 illustrates layers of an abdominal wall that may be treated using tissue matrix products 10 in accordance with the present disclosure. Although the device is illustrated as being implanted in a specific site position, one skilled in the art will recognize that the device 10 could also be implanted at other sites including inlay, onlay, retromuscular, preperitoneal, intraperitoneal or at other sites.

Figure 8:
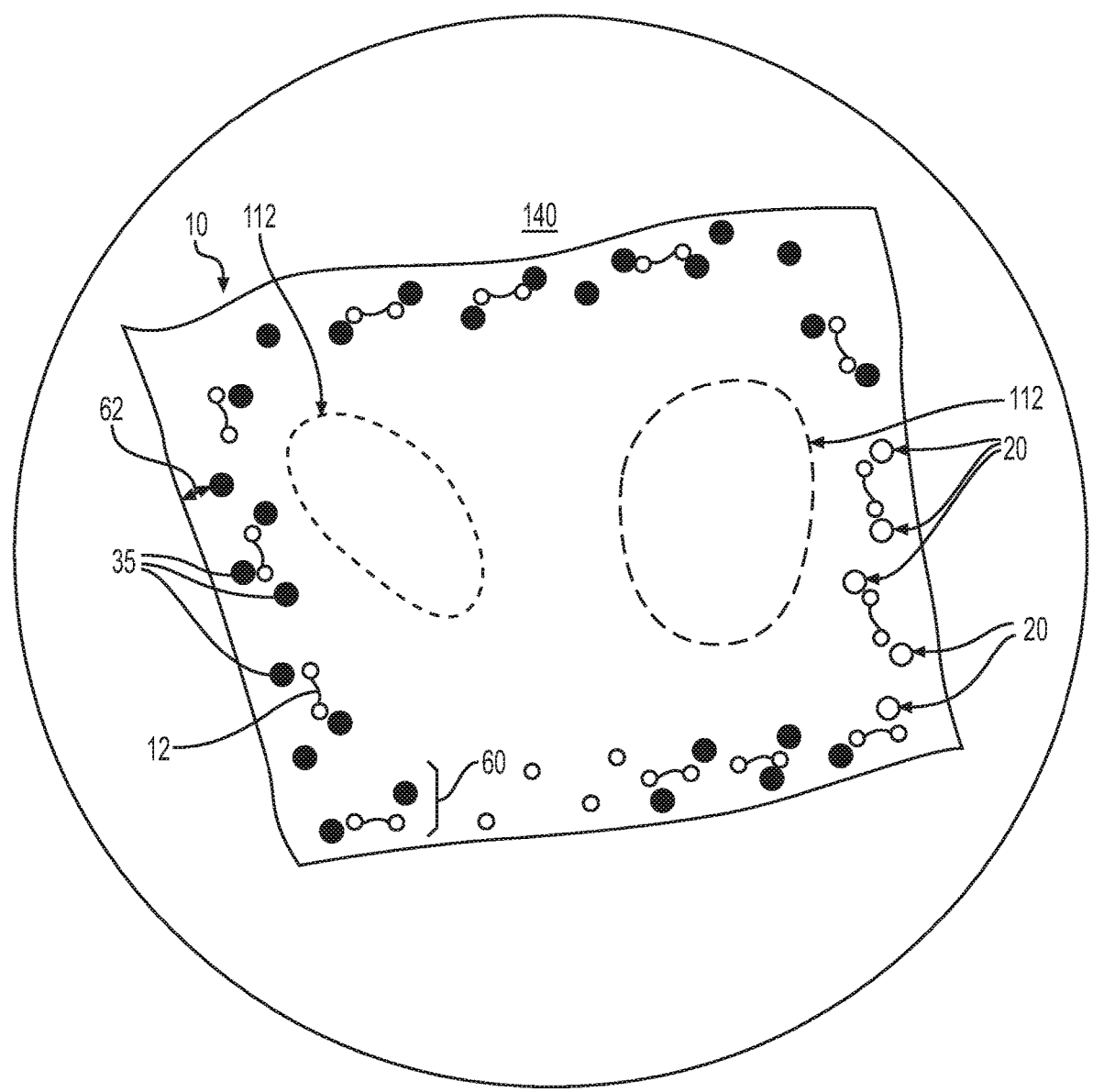
FIG. 8 depicts a tissue wall during a laparoscopic procedure treated using tissue matrix products of the present disclosure.

FIG. 8 depicts a tissue wall during a laparoscopic procedure treated using tissue matrix products of the present disclosure. As shown, the device 10' can be implanted at an anatomical site 140. In some embodiments, the anatomical site 140 can be an incision or a hernia opening. The device 10' can be placed over a wound closure 112 at the anatomical site 140 to provide structural reinforcement. After an assessment of the defect or incision to be treated, an appropriately sized tissue matrix product can be chosen to cover the defect or incision. In some procedures, a surgeon may choose to close the defect or incision. In accordance with various embodiments, the device 10' can be introduced to the surgical space by passing it through a trocar or skin incision. In an exemplary embodiment, the device 10 can be rolled to fit through a trocar in a laparoscopic procedure. In such embodiments, the device 10' can be unfurled and positioned on the abdominal wall to cover the defect or incision. The device 10' can be fixated to the abdominal wall using a variety of methods including sutures, tacks, adhesives, or any suitable combination thereof. In some embodiments, the device 10' can be manipulated with the end of a tacker tool or other laparoscopic tool. The openings 20 in the tissue (whether divots or through holes) can provide a point of purchase to allow the tacker to manipulate the device 10' into place. In some embodiments, the device 10' can be manipulated throughout the fixation process to ensure that it is positioned properly and with as much apposition to the abdominal wall as desired. In some embodiments, the surgeon can position the device 10' to minimize wrinkling.

In accordance with various embodiments, the method of treatment can include placing a suture 12 through one or more openings 20 positioned around the periphery of the device 10'. In some embodiments, between one and six spaced-apart transfacial sutures 12 can be applied on the device 10 to crudely position the device in place. In some embodiments, the sutures 12 can include mattress stitches, simple interrupted stitches, simple continuous (i.e., "baseball") stitches, or any other style or pattern of stitches as appropriate for a particular application. The method of treatment can also include placing tacks 35 in the one of more of the pilot openings 20. The tacks 35 can be single-prong or multi-prong tacks in various embodiments.

In accordance with various embodiments, the pilot openings 20 can be positioned within a perimeter region 60 of the device 10'. The perimeter region 60 can be sized to allow an area for passage of sutures or other connection devices. In various embodiments, the perimeter region 60 may extend inward from an edge of the product 10' by about 0.5 cm, 0.25 cm-0.75 cm, 0.25 cm-2.0 cm, or values in between. Larger or smaller perimeter regions 60 can be used. In various embodiments, the openings 20 can be placed with each opening 20 about the same distance 62 from the edge of the tissue product or with different distances 62 from the edge of the tissue product for each opening 20. In some embodiments, the openings 20 can be arranged in various patterns such as a "double crown" pattern. In some embodiments, the pattern can be chosen to minimize stress on the device 10' or to improve apposition of the tissue matrix 10 with the underlying tissue. The openings 20 can have properties similar to the openings 20 described above with reference to FIGS. 1A-2O.

Figure 9:
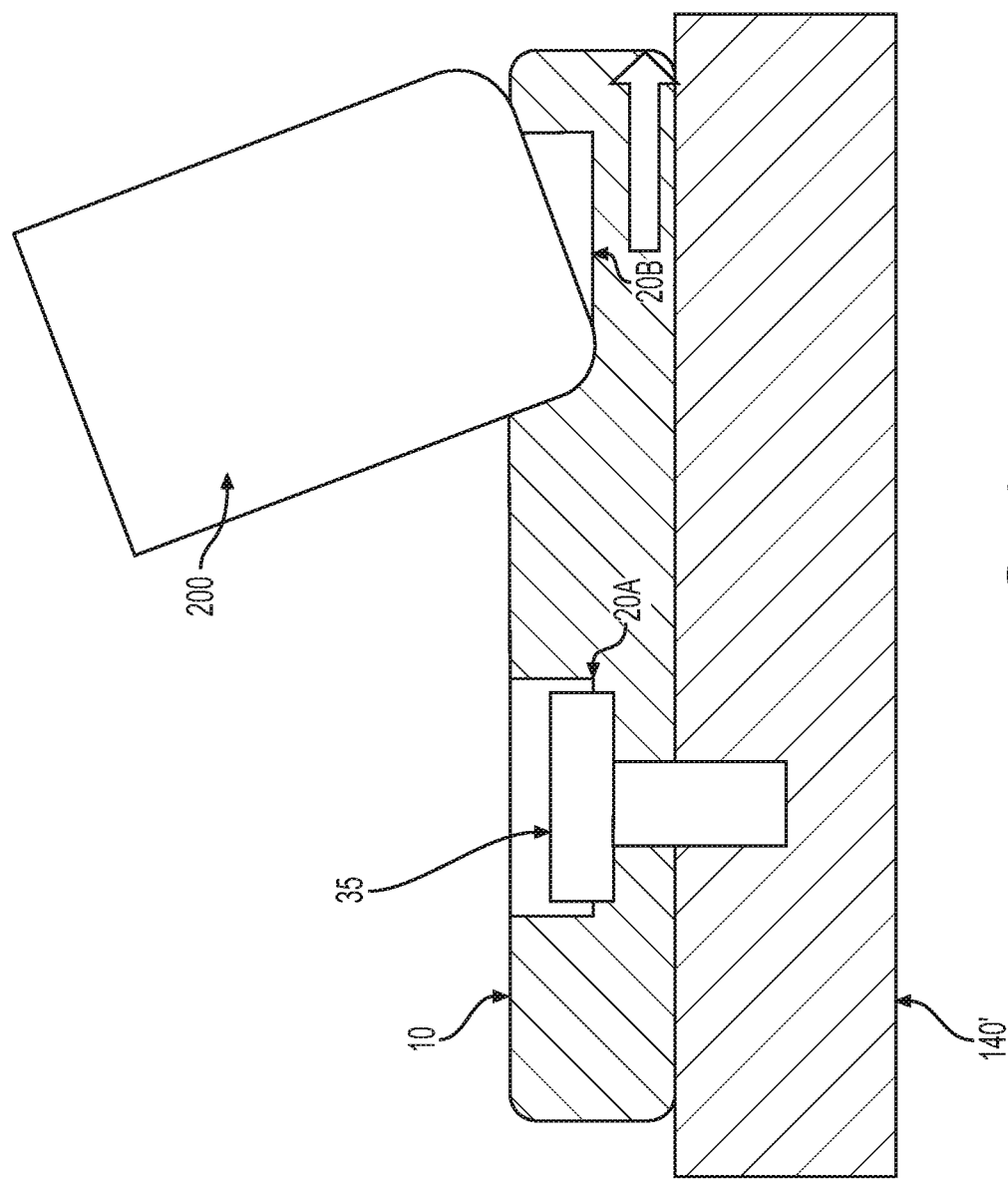
FIG. 9 depicts a tissue matrix product undergoing fixation in accordance with embodiments of the present disclosure.

FIG. 9 depicts a tissue matrix product undergoing fixation in accordance with embodiments of the present disclosure. In some embodiments, a tack 35 or suture can be placed in a first opening 20A such as a divot. The tip of a tacker 200 can be placed into a second opening 20B. Force can be applied using the tacker 200 in an outward direction away from the first opening 20A. The applied force can flatten the tissue matrix and reduce wrinkling. Finally, a tack 35 can be placed in the second opening 20B. In some embodiments, this process is repeated to flatten the tissue matrix and reduce wrinkles near any edge or corner.

The tissue matrix products can be implanted during open surgeries, during laparoscopic surgeries, or using any suitable surgical approach. The openings can be used to receive sutures, clips, staples, or other fixation devices that facilitate positioning and securing the device or surrounding tissues in place.

FIGS. 10A and 10B depict perspective and side views, respectively, of a tissue matrix product 10' having a raised portion 23 surrounding an opening 20 in accordance with various embodiments of the present application. The raised portion 23 can act as a tactile feature to indicate to a user the location of the hole. In this way, the raised portion 20 can be a marking as described previously. In addition, the raised portion 23 can help position a tacking device with respect to the opening or provide additional purchase for a tack.

Although the raised portion 23 is shown as surrounding the opening 20, the raised portion 23 can also surround only a portion of the opening 20 and can directly abut the opening 20 or can be set away from the opening 20 such that there is a distance between the raised portion 23 and the opening 20. The raised portion 23 can be produced by a variety of methods including, but not limited to, deposition of material, removal of surrounding material, or other techniques.

FIG. 11A depicts a perspective view of a portion of a tissue matrix product 10 having a ridge 61 and a trough 63 in accordance with embodiments of the present disclosure. In some embodiments, the ridge 61 or trough 63 can act as a tactile feature to indicate information to the user including orientation and spatial information such as distance of a tool from an edge of the tissue matrix product 10. In various embodiments, the ridge 61 or trough 63 can be inside the perimeter region, outside the perimeter region, or both. In an exemplary embodiment, the ridge 61 or trough 63 can help a user tack the edge of the tissue matrix product to increase apposition of the tissue matrix product to a tissue of a patient.

The tissue matrix product 10 can have either a ridge 61 or trough 63 or both a ridge 61 and trough 63 in various embodiments. In some embodiments, the plurality of openings can be adjacent the ridge 61 or trough 63 or can be spaced apart from the ridge 61 or trough 63. In some embodiments, the plurality of openings can be positioned within the ridge 61 or trough 63.

As shown in FIG. 11B, a tacker 200 can be used to smooth out the tissue matrix product 10 to increase apposition of the tissue matrix product 10 to an anatomical treatment site. This can overcome the tendency of some tissue matrix products 10 to curl at the edge. In embodiments with the ridge 61 or trough 63, the tacker 200 can find increased purchase on the tissue, and pressure applied by the tacker 200 to the sides of the ridge 61 or trough 63 can be used to smooth out the tissue matrix product 10.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

What is claimed is:

1. A method of treatment, comprising:
   selecting an anatomical site for treatment;
   selecting a tissue matrix product comprising a flexible sheet including an acellular tissue matrix, wherein the flexible sheet includes a group of openings, each opening passing partially through the acellular tissue matrix in a perimeter region of the acellular tissue matrix; and implanting the tissue matrix product in or on the anatomical site,
wherein an area surrounding or next to each opening is reinforced.

2. The method of claim 1, wherein the perimeter region extends inward from an edge of the flexible sheet by 1.5 cm.

3. The method of claim 1, wherein each opening includes a counter bore or countersink configuration.

4. The method of claim 1, wherein each opening in the group of openings is a divot.

5. The method of claim 1, further comprising securing the tissue matrix product to tissue.

6. The method of claim 1, wherein each opening has a maximum dimension between about 0.5 mm and 2 mm.

7. The method of claim 1, wherein a distance between adjacent openings is between 0.5 cm and 3 cm.

8. The method of claim 1, wherein a distance between each opening and an edge of the flexible sheet is between 0.25 cm and 1.5 cm.

9. The method of claim 1, wherein each opening is circular or comprises a slit, cruciate, or star design.

10. The method of claim 1, wherein a trajectory of each opening is normal to a surface of the flexible sheet.

11. The method of claim 1, wherein a location of at least one opening on the tissue matrix product is indicated using a marking.

12. The method of claim 11, wherein the marking is created using at least one of ink and laser engraving.

13. The method of claim 11, wherein the marking comprises a raised or depressed feature.

14. The method of claim 1, wherein the tissue matrix product further comprises at least one of a ridge or trough.

15. The method of claim 1, further comprising closing the anatomical site after implanting the tissue matrix product.

16. The device of claim 1, wherein the flexible sheet is configured to be rolled to fit through a laparoscopic trocar or cannula for insertion into a patient.

17. The device of claim 1, wherein the acellular tissue matrix is derived from human, porcine, ovine, bovine, or other animal tissue.

18. A device for use in a surgical procedure, comprising:
a tissue matrix product comprising a flexible sheet including an acellular tissue matrix,
wherein the flexible sheet includes a group of openings, each opening passing partially through the acellular tissue matrix in a perimeter region of the acellular tissue matrix,
wherein an area surrounding or next to each opening is reinforced.

19. The device of claim 18, wherein the perimeter region extends inward from an edge of the flexible sheet by 1.5 cm.

20. The device of claim 18, wherein each opening includes a counter bore or countersink configuration.

21. The device of claim 18, wherein each opening of the group of openings is a divot.

22. The device of claim 18, wherein each opening has a maximum dimension between about 0.5 mm and 2.0 mm.

23. The device of claim 18, wherein a distance between adjacent openings is between 0.5 cm and 3.0 cm.

24. The device of claim 18, wherein a distance between each opening and an edge of the flexible sheet is between 0.25 cm and 1.5 cm.

25. The device of claim 18, wherein each opening is circular or comprises a slit, cruciate, or star design.

26. The device of claim 18, wherein a trajectory of each opening is normal to a surface of the flexible sheet.

27. The device of claim 18, wherein a location of at least one opening on the tissue matrix product is indicated using a marking.

28. The device of claim 27, wherein the marking is created using at least one of ink and laser engraving.

29. The device of claim 27, wherein the marking comprises a raised or depressed feature.

30. The device of claim 18, wherein the tissue matrix product further comprises at least one of a ridge or trough.

* * * * *

UNITED STATES PATENT AND TRADEMARK OFFICE
CERTIFICATE OF CORRECTION

| | | |
|---|---|---|
| PATENT NO. | : 10,869,745 B2 | Page 1 of 1 |
| APPLICATION NO. | : 15/724616 | |
| DATED | : December 22, 2020 | |
| INVENTOR(S) | : Dennis Y. Lee et al. | |

It is certified that error appears in the above-identified patent and that said Letters Patent is hereby corrected as shown below:

In the Claims

At Column 15, Claim number 16, Line number 36, please replace "The device of claim 1" with --The method of claim 1--.

At Column 16, Claim number 17, Line number 1, please replace "The device of claim 1" with --The method of claim 1--.

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*